| United States Patent [19] | [11] Patent Number: | 4,789,735 |
|---|---|---|
| Frank et al. | [45] Date of Patent: | Dec. 6, 1988 |

[54] **CONJUGATE CONSTITUTED FROM A WALL ADHESIN OF *S. MUTANS* OF PROTEINIC NATURE AND FROM A POLYSACCHARIDE OF *S. MUTANS*, ITS PREPARATION AND ITS USE PARTICULARLY IN ANTI-CARIES VACCINES**

[75] Inventors: Robert Frank, Strasbourg; Jean P. Klein, Breuschwickersheim, both of France; Fabienne Ackermans; Hervé Bazin, both of Brussels, Belgium

[73] Assignees: Universite Catholique de Louvain, Louvain La Neuve, Belgium; Institut National de la Sante et de la Recherche Medicale, Paris, France

[21] Appl. No.: 862,919

[22] Filed: May 13, 1986

[30] Foreign Application Priority Data

May 14, 1985 [FR] France .................................. 85 07315

[51] Int. Cl.$^4$ ...................... C07K 15/04; A61K 39/09
[52] U.S. Cl. .................................... 530/395; 530/402; 530/403; 530/405; 530/806; 424/88; 424/92; 514/54; 514/23; 536/1.1; 536/123
[58] Field of Search ............... 530/395, 402, 403, 405, 530/806; 424/88, 92; 514/54, 23; 536/1.1, 123

[56] References Cited

U.S. PATENT DOCUMENTS

| 4,442,085 | 4/1984 | Colman et al. | 424/85 |
|---|---|---|---|
| 4,521,513 | 6/1985 | Russell | 435/68 |
| 4,594,244 | 6/1986 | Lehner et al. | 424/92 |
| 4,619,828 | 10/1986 | Gardon | 424/92 |
| 4,693,888 | 9/1987 | Miyaharu et al. | 424/88 |

FOREIGN PATENT DOCUMENTS

| 90617 | 5/1983 | European Pat. Off. | |
|---|---|---|---|
| 0116472 | 8/1984 | European Pat. Off. | 424/92 |

OTHER PUBLICATIONS

Bacterial Vaccine, ed., Germanier, 1984, Academic Press (see p. 250).
Makela, et al., *Scand. J. Immunol*, 19, 1984, pp. 541–550.
Taubman, et al., *J. Dental Res.* 60, 1981, p. 634 (#1298).
Wachsmann, et al., *Infect & Immunity*, 52, 1986, pp. 408–413.
Bruyere, et al., *Vaccines*, 5, 1987, pp. 39–42.

*Primary Examiner*—J. R. Brown
*Assistant Examiner*—Garnette D. Draper
*Attorney, Agent, or Firm*—Fleit, Jacobson, Cohn & Price

[57] ABSTRACT

The conjugate according to the invention is constituted by a wall adhesin of *Streptococcus mutans*, of a proteinic nature, capable of binding the components of saliva, or an active fraction of such a protein, covalently coupled to a *Streptococcus mutans* polysaccharide, or to a fraction of such a polysaccharide.

Preferably, the adhesin is constituted by a single polypeptide chain having a molecular weight of about 74,000; it is common to the different serotypes of *Streptococcus mutans* where it has a crossed antigenicity; and it is capable of interacting with the salivary glycoproteins and polysaccharide derived from the same serotype of *S. mutans*, particularly serotype f.

Use for the preparation of immunogenic compositions, particularly for the preparation of vaccines against dental caries.

12 Claims, No Drawings

CONJUGATE CONSTITUTED FROM A WALL ADHESIN OF S. MUTANS OF PROTEINIC NATURE AND FROM A POLYSACCHARIDE OF S. MUTANS, ITS PREPARATION AND ITS USE PARTICULARLY IN ANTI-CARIES VACCINES

The invention relates to a product obtained by covalent linking of a protein with a polysaccharide, its preparation and its use.

More precisely, the invention relates to a product in which a wall adhesin of *Streptococcus mutans*, of proteinic nature, or a fraction of such a protein, is covalently linked to a *Streptococcus mutans* polysaccharide, or to a fraction of such a polysaccharide, a process for its preparation and its use as an antigen, particularly in vaccines against dental caries.

*Streptococcus mutans* is considered at the present time to be the principal bacterium responsible for caries disease in man and in animals. This bacterial species is formed by 8 different serotypes bearing the references a to h.

In the course of the last few years, numerous immunization experiments, using this bacterium as an antigen, have shown the possibility of obtaining protection against caries lesions, by means of such an antigen. However the use of this complete bacterium seems to result in undesirable cross reactions with other tissues such as the cardiac tissue, and this is why the present work is principally oriented towards the research for simple antigens, derived from this bacterium, and possessing the same protective capability.

The principal characteristics of *Streptococcus mutans* are the power to adhere to the acquired exogenic pellicle formed at the surface of the tooth principally by adsorbed salivary glycoproteins, and this by means of wall adhesins of a proteinic or polysaccharide nature, and to synthesize, by means of enzymes, the glucosyltransferase (GTFs), dextrans which ensure the cohesion of the bacteria at the level of the dental plaque.

The possibility of inhibiting the fixation and aggregation of the *Streptococcus mutans* on the tooth has been studied by numerous authors in the course of immunization experiments using GTFs as antigens. However the results obtained do not permit a conclusion as to the effectiveness of such an antigen, perhaps by reason of the very great polymorphism of GTFs of *Streptococcus mutans*.

On the other hand, the use of certain proteins purified from supernatants of *Streptococcus mutans*, that is to say excreted by this bacterium, of which the biological role is unknown, has given rise to encouraging results in the course of animal immunization experiments.

Another possibility of acting on the colonization of the dental surfaces would be to block the adherence of *Streptococcus mutans* by inducing the synthesis of antibodies against the wall adhesins capable of interacting with the salivary glycoproteins.

This solution has already been envisaged but until now has not led to satisfactory results. Thus, it has been observed that the polysaccharides of various serotypes, although taking part in the adherence process, are practically incapable of inducing lasting immune responses.

Certain authors have in addition proposed the use as antigens of wall adhesins of proteinic nature; thus for example in patent application EP No. 116 472. More encouraging results have thus been obtained.

It is an object of the invention to perfect a product comprising a *Streptococcus mutans* wall adhesin, of a proteinic nature, capable of inducing stronger and/or more lasting immune responses than those which are induced by adhesin itself.

This purpose has been achieved according to the invention which provides particularly a conjugate constituted by a *Streptococcus mutans* wall adhesin, of a proteinic nature, capable of binding the components of the saliva, or by an active fraction of such a protein, coupled covalently to a *Streptococcus mutans* polysaccharide, or to a fraction of such a polysaccharide.

The covalent linkage is effected by methods known in themselves, useful in biology and compatible with the structure of the protein on the one hand and the polysaccharide on the other hand. It can particularly be carried out by means of an "arm" introduced in a manner known in itself and bringing into action bifunctional reagents such as carbodiimids, for example.

However, the "arm" inserted in the structure of the product can possibly lead to the formation of undesirable specific antibodies, so it may be preferable not to resort thereto to establish the covalent linkage.

According to a preferred embodiment, the covalent linkage is effected by controlled oxidation of the polysaccharide, particularly by sodium periodate, followed by coupling with the protein by reducing amination in the presence of sodium borohydride.

The wall adhesin of proteinic nature which is contained in the cellular wall extract of bacteria (cell Wall Extracted Antigen: WEA) may be obtained by any method described in the literature, in particular by the method of M. Schöller et al. described in Infect. Immun. 31, 52–60 (1981) or by analogy with this method, for example as described by J. A. Ogier et al. in Infect. Immun. 45 (1), 107–112 (1984).

It may be also advantageous to use only an active fraction of such an adhesin, that is to say a fraction capable of binding the components of the saliva and inducing antibodies, obtained by fractionation of an adhesin prepared as indicated above, by chemical synthesis or again by genetic engineering.

The *Streptococcus mutans* polysaccharide can be obtained particularly by the method of S. Hamada et al. described in Molec. Immunol. 20, 453 (1983).

It may also be advantageous to use only an active fraction of such a polysaccharide, that is to say a fraction capable particularly of binding the components of the saliva.

The wall adhesin of proteinic nature, or its fraction, used comes preferably from the same serotype as the polysaccharide or the polysaccharide fraction used. However, taking into account the crossed antigenicity observed with the majority of adhesins of proteinic nature, it is also possible to combine an adhesin and a polysaccharide coming from different serotypes, or fractions thereof.

The conjugate so obtained, particularly when it is administered orally to animals, in particular in association with liposomes, results in IgA responses in the saliva and the serum superior to those obtained with the uncoupled protein. It is recalled in this respect that the IgAs are immunoglobulins capable of protecting against dental caries (see M. A. Taubman et al. in J. Dent. Res. 60, 634 (1981)).

The conjugate according to the invention is in addition capable of inducing a local and systemic IgA response directed against the polysaccharide used whereas the same polysaccharide, administered under the same conditions, particularly in association with liposomes, is unable to induce any IgA response.

This is all the more surprising since it had been shown generally, that the conjugation of different bacterial polysaccharides with proteins by different methods, increased their immunogenicity by inducing an anti-polysaccharide IgG response (see for example E. C. Beuvery et al., Infect. Immun. 40, 39 (1983) and O. Mäkelä et al., Scand. J. Immunol. 19, 541 (1984)) whereas with the conjugate according to the invention the IgG response is weak.

Finally, the conjugate according to the invention confers, just as its proteinic constituent, an "immunological memory", whereas the polysaccharide alone is devoid of this property.

Taking into account all of its properties, the conjugate according to the invention may be used in various applications as an antigen, and in particular as a compound with immunogenic activity. Moreover, and especially, it may be used, alone or in admixture with other antigens of the same type or with *Streptococcus mutans* wall adhesins, particularly of a proteinic nature, in vaccines against dental caries.

Taking into account the various serotypes of *Streptococcus mutans* existing, it may be advantageous to use together different conjugates in which at least the wall adhesins of proteinic nature come from different serotypes of *Streptococcus mutans*.

According to an advantageous embodiment, the conjugate according to the invention comprises a wall adhesin of proteinic nature, recently isolated, called below 74K SR(SR=Saliva Receptor: receptor of saliva), which is characterized in that:

it is constituted by a single polypeptide chain having a molecular weight of about 74,000;

it is common to different serotypes of *Streptococcus mutans* where it shows a crossed antigenicity; and it is capable of interacting with salivary glycoproteins.

This protein may be prepared from a strain of *S. mutans* of serotype f, of human origin, by extraction of crude antigens associated with the cell wall of the bacteria, by means of 0.5M phosphate buffer, pH 6.0 and purification by immunoaffinity chromatography by means of a monoclonal antibody directed against the proteins interacting with the salivary glycoproteins, in the presence of a non ionic detergent and sodium dodecylsulfate, with elution by NaCl or glycine/HCl buffer.

The details of this preparation will be given in the examples which follow.

The antigen 74K SR, of a proteinic nature, is a novel product capable by itself alone of inducing a local and systemic IgA response and of conferring a "immunological memory". It can hence be used as active principle in compositions with immunogenic activity, in particular in vaccines against dental caries.

However as has been indicated above as regards the wall adhesins of *S. mutans* of a proteinic nature in general, the coupling of the 74K SR antigen with a polysaccharide of *S. mutans* enables a conjugate to be obtained having superior properties.

The polysaccharide used comes advantageously from the same strain of *S. mutans* serotype f as the antigen 74K SR. This polysaccharide, which is prepared, for example, by the method of Hamada et al. indicated above, is called below "poly f".

In a preferred embodiment, the conjugate according to the invention is constituted from the 74K SR antigen bonded covalently, by reducing amination, to the poly f, after controlled oxidation of the latter.

Whatever its composition and its method of production, the conjugate according to the invention can be used as an antigen, for example, in methods of separation of antibodies or in assays.

It can also advantageously be used in preparations with immunological activity, particularly for the preventin of dental caries, such as, for example, toothpastes, chewing-gums etc.

Finally and particularly, it can be used as an active principle in a vaccine against dental caries.

Although different routes of administration of the vaccine such as local treatment or injection could be envisaged, it seems quite desirable that the vaccine should be in the form of a pharmaceutical preparation intended for oral administration. It is in particular desirable that this pharmaceutical form should be such as to permit the conjugate to exert its action at the level of the Peyer's patches and the mesenteric lymph nodes.

To do this, the conjugate according to the invention or a mixture of conjugates of this type, possibly in the presence of other antigens, can advantageously be associated with an adjuvant such as particularly muramyl-dipeptide (MDP) or liposomes, according to known techniques.

The pharmaceutical forms used can include various customary excipients, particularly for a delayed action.

By way of indication, a dose of vaccine administered to man can contain from 1 to 100 mg of the conjugate according to the invention.

Tests on animals have shown that at effective doses, the conjugate according to the invention shows no toxicity.

It seems that a more efficient protection is obtained if the vaccination is followed by several boosters, for example three, at intervals of some months.

The invention will be better understood by means of the detailed examples and of the description of the pharmacological tests which follow.

EXAMPLE 1

Preparation of the 74K SR antigen

*Streptococcus mutans* OMZ 175 (serotype f), whose preparation is described by B. Guggenheim in Caries Res. 2, 147–163 (1968) is cultivated in a liquid medium (brain-heart broth marketed under the name "Brain-Heart Infusion Broth" of the Difco Laboratories Company, Detroit U.S.A.). The cells are harvested after 12 hours of culture at 37° C., washed and extracted with 0.5M phosphate buffer, pH 6.0 by the method described by M. Schöller et al. in Infect. Immun. 31, 52–60 (1981). The bacterial extract in the phosphate buffer is then dialysed according to the usual methods and used for the separation of the 74K SR antigen.

This purification is effected by means of immunoaffinity chromatography on an agarose gel column marketed under the name Sepharose CL 4B (Pharmacia, Uppsala, Sweden) activated with cyanogen bromide and coupled with a monoclonal antibody directed against proteins interacting with salivary glycoproteins (namely 8 to 10 mg of antibody/ml of gel) whose preparation is indicated below. The column is equilibrated with 0.01M TRIS/HCl (pH 7.2)/NaCl 0.15M (TS buffer).

The antigen extract extracted from the cell wall (WEA) as purified above is chromatographed on this column. About 30 mg of extract in Tris buffer containing 1% of non-ionic detergent marketed under the name Triton X-100 and 0.05% of sodium dodecylsulfate (SDS) are applied to the column. It is rinsed with TS buffer. The material specifically bonded is eluted either with 5M NaCl, or with 0.2M glycine/HCl, pH 2.8 and is immediately neutralized with 1M Tris. After removal of the elution agent by dialysis against TS buffer at 4° C., the purity of the protein is checked by electrophoresis in polyacrylamide gel.

The only protein recovered after elution under these particular conditions has a molar mass in the vicinity of 74 kDa and represents about 27 to 31% of the total bonding activity with salivary glycoproteins of the proteins chromatographed; this is the protein 74K SR.

Production of the specific monoclonal antibodies of the antigens associated with the cell wall The extract of antigens associated with the cell wall is obtained as described above with inactivation of the proteases according to the method of R. R. B. Russell et al. described in J. Gen. Microbiol. 129, 865–875 (1983). The crude protein fraction is chromatographed on an acrylamide column marketed under the name Bio-Gel P6 of the Bio-Rad Laboratories Company (Richmond, Calif., USA), and adjusted to a final concentration in proteins of 2 mg/ml.

Production of antibody secreting hybridomas

Rats of the Wistar strain are immunized intraperitoneally with 50 μg of proteinic fraction percipitated with alum, twice, at a 14 day interval. Seven months later, the rats receive a booster of 100 μg of WEA intravenously, in phosphate buffer saline (PBS). The spleen cells are collected 4 days later and fused with myelomatous cells of Lou strain rats not secreting IR 983F [see the article of H. Bazin in Prot. Biol. Fluids 29, 615–658 (1982)] in a cell ratio of 5 to 1. The fusion solution is polyethyleneglycol 4000 of the Merck Company (Darmstadt, RFA) and the culture is grown in the presence of modified Eagle type nutrient medium in wells of culture plates. About two weeks after the fusion, the antibodies against the WEA antigens are sought in the wells which have undergone a growth of hybrid cells, by indirect solid phase radioimmunological assay. The positive clones are recloned under the usual conditions, at least twice, to ensure the "monoclonality" and, by transfer onto nitrocellulose paper (so-called "Western Blot" technique), the hybridomas producing antibodies directed against the proteins interacting with salivary glycoproteins are selected.

Production of ascitic fluid and antibody purification

Hybridoma cells of monoclonal origin are injected intraperitoneally into hybrid rats (Wistar R/Lou C) F1, the ascites liquid is collected and the immunoglobulin purified.

Each monoclonal antibody of IgM type is precipitated from the ascites liquid clarified by dialysis against 0.1M Tris-HCl buffer, pH 8 (48 hours, 4° C.). Radial immunodiffusion of the supernatants reveals a 100% removal of the antibody from each ascite. The protein is dissolved in PBS, pH 7.2, applied to a 5 m Biol-Gel A column (90×2.6 cm) of the Bio-Rad Laboratories Company, and eluted with PBS buffer. The IgM peak is recovered, adjusted to a final protein concentration of 4 mg/ml and stored at −80° C.

EXAMPLE 2

Preparation of the polysaccharide of serotype f (poly f)

This polysaccharide is prepared by the method of Hamada et al. described in Molec. Immunol. 20, 453 (1983) from lyophilized cells of *S. mutans* OMZ 175.

In summary, the cells are suspended in PBS pH 7.4 and autoclaved for 30 minutes at 120° C. The supernatant is dialysed against distilled water and chromatographed on a column marketed under the name DEAE Trisacryl M of the IBF Company (France) equilibrated with 0.01M TRIS/HCl buffer (pH 7.4). The unadsorbed material is again chromatographed on a Bio-Gel P100 column of the Bio-Rad Company and the fractions eluted in the void volume of the column, after dialysis against water and lyophilization, are constituted by the polysaccharide of *S. mutans* of serotype f or poly f.

EXAMPLE 3

Coupling of the poly f and of the 74K SR protein: production of the preferred conjugate according to the invention The conjugate is prepared by the method of Sanderson et al. described in Immunology, 20, 1061 (1971). 20 mg of poly f are oxidized with 4 ml of 0.1M sodium periodate solution (pH 4.5) for 1 hour, at room temperature and in the dark. The oxidized poly f is purified by elution with water on a Bio-Gel P100 column (1.6×20 cm) and freeze-dried. The oxidized poly f is then coupled to 6 mg of 74K SR antigen purified by reducing amination with sodium borohydride, according to the method of I. Parikh et al. described in Methods in Enzymology, vol. XXXIV, (Academic Press) p. 77–102 (1974). After removal of the excess reagent by chromatography on a Bio-Gel P6 column (Bio-Rad), the crude conjugate is applied to a DEAE Trisacryl M column (1.6×10 cm) equilibrated with 0.01M Tris/HCl buffer (pH 7.4). After removal of the uncoupled poly f, the poly f-74K SR conjugate is eluted with 0.01M Tris/HCl buffer containing 1M NaCl. This fraction, after dialysis against PBS, is again freed from unreacted proteins by chromatography on an immuno-adsorbant anti poly f. The purified conjugate is eluted from the immuno-adsorbant by means of 0.1M acetate buffer (pH 4.0) and is immediately neutralized with 1M phosphate buffer (pH 7.4). After removal of the elution agent by chromatography on Bio-Gel P6, the purified conjugate is concentrated by freeze-drying.

On the basis of the determinations of the hexoses (D. L. Morris, Science 107, 254 (1948)) and the concentration of proteins (O. H. Lowry et al. J. Biol. Chem., 193, 265 (1951)), it is observed that the molecular ratio of the poly f to the 74K SR protein in the conjugate is 1:0.8.

Pharmacological study of the poly f-74K SR protein conjugate

The effectiveness of the poly f-74K SR protein conjugate as an antigen has been compared, in the course of an experiment on the rat, on the one hand with the immunogenicity of the poly f alone and on the other hand with the immunogenicity of the 74K SR protein alone.

The results obtained show that the immunization of the animals by the conjugate leads to a strong salivary immune response of the IgA type, directed both against the poly f and the protein, as against the absence of salivary IgA immune response obtained with the polysaccharide alone. The immunogenicity of the coupled protein is in addition superior to that of the protein alone.

In conclusion, the coupling of a wall adhesin of an *S. mutans* to a polysaccharide of *S. mutans* increases its antigenicity and leads to a strong local immune response.

In addition, this coupling enables the induction of a "immunological memory" against two types of surface receptors very important in the formation of dental plaque, namely adhesions of proteinic nature on the one hand, and adhesions of polysaccharide type on the other hand.

Finally, it has been possible to establish, by the demonstration of a crossed immunogenicity, that 74K SR protein is common to the different serotypes of *S. mutans* or at least shows a common epitope with surface proteins of the other serotypes. Consequently, a vaccine using a conjugate comprising this protein is effective against strains of *S. mutans* of different serotypes.

Examples of preparation of a vaccine according to the invention: Liposomes containing the conjugate according to the invention as antigen The preparation of these liposomes may be carried out by the method of G. Gregoriadis described in Biochem. J. 129, 123 (1971). In particular, according to the indications of D. Wachsmann et al. in Immunology 54 (1), 189–194 (1985), the conjugate being incorporated into small unilamellar liposomes composed of phosphatidyl choline, cholesterol and phosphatidic acid (molar ratio 7:2:1).

We claim:

1. A conjugate comprising a proteinic *Streptococcus mutans* wall adhesin covalently coupled to an *S. mutans* polysaccharide, said wall adhesin being capable of binding the components of saliva and consisting of a single polypeptide chain, common to the different *S. mutans* sterotypes, with a molecular weight of about 74,000.

2. A conjugate according to claim 1, wherein the proteinic acid adhesin is capable of binding salivary glycoproteins.

3. A conjugate according to claim 1, wherein said wall adhesin and said polysaccharide are extracted from the same serotype of *S. mutans*.

4. A conjugate according to claim 3, wherein said wall adhesin and said polysaccharide are extracted from *S. mutans* serotype f.

5. A conjugate according to claim 4, wherein said wall adhesin and said polysaccharide are extracted from the same strain of *S. mutans*, serotype f.

6. A conjugate according to claim 1, wherein the conjugate is obtained by coupling said polysaccharide, after controlled oxidation with sodium periodate, to said wall adhesin protein through reductive amination in the presence of sodium borohydride.

7. A process for protecting against caries lesions comprising the use of the conjugate according to claim 1 as antigen.

8. A vaccine against dental caries comprising, as active principle, an effective amount of a conjugate according to claim 1, together with an adjuvant.

9. A vaccine according to claim 8 in an orally administrable galenic form.

10. A vaccine according to claim 9, wherein the adjuvant is muramlydipeptide.

11. A vaccine according to claim 8, wherein the adjuvant consists of liposomes into which the conjugate has been incorporated.

12. A vaccine according to claim 8 which contains from 1–100 mg of a conjugate according to claim 1.

* * * * *